United States Patent [19]

Valencia

[11] Patent Number: 5,624,975
[45] Date of Patent: Apr. 29, 1997

[54] PLASTICS

[75] Inventor: Gregorio P. Valencia, Barcelona, Spain

[73] Assignee: Biocompatibles Limited, London, England

[21] Appl. No.: 193,638

[22] Filed: Feb. 7, 1994

Related U.S. Application Data

[63] Continuation of Ser. No. 789,892, Nov. 12, 1991, abandoned, which is a continuation of Ser. No. 582,124, Sep. 13, 1990, abandoned, which is a continuation of Ser. No. 205,497, Jun. 7, 1988, abandoned, which is a continuation of Ser. No. 926,729, Nov. 4, 1986, abandoned.

[30] Foreign Application Priority Data

Nov. 4, 1985 [GB] United Kingdom ............ 8527071

[51] Int. Cl.$^6$ ................ C08L 15/00; C08K 5/52
[52] U.S. Cl. ............ 523/111; 524/145; 424/486; 424/487
[58] Field of Search ............ 523/111; 524/145; 424/486, 487

[56] References Cited

U.S. PATENT DOCUMENTS

| | | | |
|---|---|---|---|
| 2,576,576 | 11/1951 | Cresswell et al. | 128/335.5 |
| 4,091,170 | 5/1978 | Godfrey. | |
| 4,152,316 | 5/1979 | Cooper et al. | 524/141 |
| 4,348,329 | 9/1982 | Chapman | 556/406 |
| 4,451,425 | 5/1984 | Meyer | 524/145 |
| 4,721,800 | 1/1988 | Chapman et al. | 556/405 |
| 5,342,621 | 8/1994 | Eury. | |

FOREIGN PATENT DOCUMENTS

| | | |
|---|---|---|
| 0086769 | 8/1983 | European Pat. Off.. |
| 48-830 | 1/1973 | Japan. |
| 50-75655 | 6/1975 | Japan. |
| 50-119853 | 9/1975 | Japan. |
| 54-2285 | 1/1979 | Japan. |
| 56-33028 | 4/1981 | Japan. |
| 56-70926 | 6/1981 | Japan. |
| 58-127653 | 7/1983 | Japan. |
| 58-224643 | 12/1983 | Japan. |
| 59-20338 | 2/1984 | Japan. |
| 8402255 | 6/1984 | WIPO. |

OTHER PUBLICATIONS

National Technical Information Service, Document No. AD–A135 268 "A Biodegradable and Proteolipid Bone Repair Composite".
Chemical Abstracts, vol. 103, 1985, 123218s.
Chemical Abstracts, vol. 96, 1982, 50361j.
Tatebe et al. Chem Abs., 96:223208g (1986).

Primary Examiner—Peter D. Mulcahy
Attorney, Agent, or Firm—Sughrue, Mion, Zinn, Macpeak & Seas

[57] ABSTRACT

Plastics materials may be plasticized using lipids as the sole plasticizer or in combination with conventional plasticizers. When appropriate lipids are used thermosetting plastics and elastomers may be rendered biocompatible or therapeutic articles and substained release medicaments may be formed.

7 Claims, No Drawings

PLASTICS

This is a continuation of application Ser. No. 07/789,892 filed Nov. 12, 1991, now abandoned, which is a continuation of application Ser. No. 07/582,124, filed Sep. 13, 1990, now abandoned, which is a continuation of application Ser. No. 07/205,497, filed Jun. 7, 1988, now abandoned, which is a continuation of application Ser. No. 06/926,729 filed Nov. 4, 1986, now abandoned.

The present invention relates to new plastics materials especially materials suitable for use in biomedical applications, articles formed from such materials and processes for modifying the physical and biological properties of plastics materials.

Thermoplastic materials are frequently employed in the construction of a wide variety of articles used in modern medicine but a great deal of medical devices are nowadays made out of either thermosettings or elastomers. Elastomers, by nature of their long-chain molecules, are able to withstand large deformations and return to their original dimensions. A number of elastomers (commonly referred as rubbers) have been tried as implant materials. These include acrylate, butyl rubber, chlorosulfonated polyethylene (Hypalon), epichlorohydrin rubber(Hydrin), natural rubber, polyurethanes(Esthane), and silicone rubber(Silastic). The thermosetting plastics, contrary to thermoplastics, cannot be melted, reshaped or reformed upon reheating because the polymerization reactions that have taken place are irreversible. Epoxy polymers are the only thermosetting materials that have been used successfully as implant materials.

A plasticiser or softener is a substance or material incorporated in a thermoplastic or an elastomer, to increase its flexibility, workability or distensibility. Plasticisers are also used to alter the physical properties, e.g. brittleness, of thermosetting plastics. A plasticiser may reduce the melt viscosity, lower the temperature of second-order transition or lower the elastic modulus of the product.

The plasticiser molecules neutralize the secondary bonds, known as van der Waal's forces, between the polymer molecules increasing the mobility of the polymer chains and reducing their crystallinity. Thus plasticisers are added to plastics mainly to improve flow, and thereby processability, and to reduce brittleness. The plasticiser added is usually required to lower the glass-transition temperature to below ambient temperature. The properties of thermoplastics then change from hard, brittle, glass like materials to soft, flexible, tough materials. To be effective and useful, a plasticiser must be compatible with the host plastic material. Since the molecular weight and size of plasticiser molecules are relatively small, when compared with high polymer molecules, the thermodynamic difficulties in mixing are not as great as with mixtures of high polymers. Nevertheless, since another requirement of a plasticiser is that it be nonvolatile and nonmigrating, substantial molecular weights are desirable and the choice of plasticisers for a given plastic is fairly narrow. Generally, plasticisers depend on polar intermolecular forces between the plasticiser and the polymer, this explains why plasticisation is difficult to achieve in nonpolar polymers, such as the polyolefins. It is also important to note that plasticisation is difficult to achieve with highly crystalline polymers. Amorphous polymers and slightly crystalline materials are most usefully plasticised.

The two major sub-groups of plasticisers are the internal plasticisers i.e. a second monomer which is copolymerised into the polymer structure, thereby making it less ordered and, therefore, more difficult for the chains to fit closely together, and the external plasticisers which are often classified into simple and resinous types. Simple plasticisers are usually individual chemical compounds whose constitution and physical and chemical properties are known. Resinous plasticisers include polyesters obtained by polymerization of unsaturated monomers, and usually contain a range of molecular weights so that their chemical constitution is not normally well known. Simple and resinous plasticisers are frequently given the alternative names monomeric and polymeric, respectively. However, alternative ways to describe them are as "low molecular weight plasticisers" and "high molecular weight plasticisers".

The majority of simple plasticisers are high-boiling esters of polybasic acids such as phthalate, phosphate, adipate and azelate esters. These substances remain in the plastic material after processing and modify its properties. Loss of plasticiser from such systems can occur by volatility, extraction by solvents, and migration into other media. This can lead to the deterioration of the physical properties of the plastic. Polymer plasticisers, which are mostly polyesters, on the other hand, are removed much less readily by these three methods by virtue of their higher average molecular weight and this type of plasticiser, therefore, exhibits a greater degree of permanence than the simple plasticisers. In general, these advantagous properties of polymeric plasticisers are offset to some extent by certain disadvantages as compared with low molecular weight plasticisers. These disadvantages include higher price, greater difficulty in handling and processing, lower plasticising efficiency, and the poorer low-temperature properties shown by the plastic composition.

Biomedical applications of polymers include use as implants, prostheses, blood or tissue contacting devices, artificial organs like blood detoxificators and oxygenators. However, there are at the present time many difficulties and problems associated with the use of these polymers, due to the incompatibility of living tissues and foreign materials artificially inserted in the body, and adverse reactions including protein deposition, adhesion and destruction of red blood cells, platelet adhesion and aggregation, and blood coagulation, can occur.

Surprisingly we have now found that lipids may be incorporated into plastics to modify the physical properties usually in the manner of an external plasticiser and may therefore replace some or all of the conventional internal or external plasticisers normally included in such plastics. Moreover by choosing appropriate lipids the biological properties of the plastics may be adjusted for instance to improve their biocompatibility, or to confer other important biomedical properties such as thromboresistance or antitumor activity.

In appropriate circumstances the lipid plasticiser may leach from the plastics material and this can be exploited by using the materials as sustained release or depot formulations of pharmacologically active lipids.

Accordingly the present invention provides a plastics material comprising a polymer and a lipid. Preferably the plastics material is suitable for use in biomedical apparatus, surgical implants and other applications where the biological properties of the plastic are important. Usually the polymer will be one that is already known for use in biomedical applications, a mixture of such polymers or a copolymer. Typical such polymers include thermoplastics such as cellophane, cellulose acetate, polyolefins, fluorinated hydrocarbons(Teflon), polyhydroxyethylmethacrylate (PHEMA) (Hydron), PMMA, polycarbonate and polyvinylchloride(PVC) and particular examples of known polymer types and their biomedical applications are given in Table I below:

TABLE 1

| POLYMER | USES |
|---|---|
| Acrylate elastomers. | Prostheses. |
| Chlorosulfonated polyethylene (Hypalon). | Vascular surfaces. |
| Pure natural rubber. | |
| Polyurethanes (Esthane)(Ostamer)(Biomer)(Pellethane)(Lycra/Spandex)(Cardiothane)(Tecoflex). | Prostheses, artificial hearts, vascular surfaces. |
| Silicone rubber (Silastic). | Artificial hearts and valves, blood oxigenator films. |
| Cellophane. | Dialysis membranes. |
| Cellulose acetate. | |
| Fluorocarbons (Teflon). | Vascular and bulk implants. |
| Polyhydroxyethylmethacrylate (PHEMA). | Contact lenses, drug delivery, catheters, suture coating, prostheses. |
| Polymethylmethacrylate (PMMA)(Lucite)(Plexiglas)(Perspex). | |
| Polyethylmethacrylate (PEMA). | |
| Polyamides (Nylon). | Sutures, fabrics. |
| Polyethyleneterephthalate (Dacron)(Terylene)(Mylar). | |
| Silk. | |
| Polymonochloro-p-xylylene. | Encapsulants of electronic components for implantation. |
| Epoxy resins. | |
| Polyethylene (Vitrathene). | Prostheses. |
| Polypropylene. | Components of blood oxygenators and dialyzers, heart valves. |
| Polyvinylalcohol (PVA). | Dialysis films. |
| Polyvinylchloride (PVC). | Blood bags, blood tubing, prostheses. |
| Polyvinylidenechloride | Vascular surfaces. |

Particular Examples of such known polymers are those in Table II below:

TABLE II

| POLYMER | Molecular Weight | Glass Transition Temperature, ($T_g$, °C.) | Density ($d$, g · cm$^{-3}$) |
|---|---|---|---|
| Poly(acrylamide) | $5 \times 10^6/6 \times 10^6$ | 165 | 1.302 |
| Poly(acrylic acid) | 250000 | 106 | |
| Poly(acrylonitrile) | | 85 | 1.184 |
| Polyamide resin | | 95/200 | 0.98 |
| Poly(1-butene) | high | | 0.91 |
| Poly(1,4-butyleneterephthalate) | | 66 | 1.31 |
| Poly(butyl methacrylate) | high | 27 | 1.07 |
| Poly(tertbutyl methacrylate) | | 107 | 1.022 |
| Poly(4-tertbutyl styrene) | | 132 | |
| Polycarbonate resin | 20000/25000 | 150 | 1.20 |
| Poly(cyclohexyl methacrylate) | | 104 | 1.100 |
| Poly(2,6-dimethyl-1,4-phenylene oxide) | | 211 | 1.06 |
| Poly(ethylene) | | | 0.92/0.95 |
| Poly(ethylene) chlorinated | | | 1.1/1.2 |
| Poly(ethylene glycol) | 3000/14000 | | 1.2 |
| Poly(ethylene oxide) | | | |
| Poly(ethylene terephthalate) | | 81 | 1.37 |
| Poly(ethyl methacrylate) | very high | 66 | 1.11 |
| Nylon 6, 6/6, 6/9, 6/10, 6/12, 11, 12 | | 37/242 | 1.0 |
| Polyimide | | 310 | 1.4 |
| Poly(isobutyl methacrylate) | high | 53 | 1.09 |
| Poly(4-isopropyl styrene) | | 87 | |
| Poly(methyl methacrylate) | low | 114 | 1.188 |
| Poly(4-methyl styrene) | | 106 | 1.04 |
| Poly(styrene) | | 100 | 1.047 |
| Polysulfone resin | | 190 | 1.24 |
| Poly(tetrafluoro ethylene) | | 130 | 2.00 |
| Poly(vinyl acetate) | | | |
| Poly(vinyl alcohol) | 115000 | 99 | 1.269 |
| Poly(vinyl butyral) | 36000 | 51 | 1.083 |
| Poly(vinyl chloride) | very high | 85 | 1.385 |
| Poly(vinyl formal) | | 108 | 1.23 |

Other biomedical applications of interest where excellent biocompatibility is important are blood carrier bags, dialysis membranes, blood oxygenator films, tubing, connectors, stoppers, closures for dialysis and oxygenation machines, adhesives, diagnostic catheters, surgical drapes and tapes, contact lenses, encapsulants for electronic devices and cell culture plastic materials.

The lipid used to modify the physical and biological properties of the polymer may be any amphipathic compound having one or more long chain saturated or unsaturated fatty side chains (e.g. fatty acids, alcohols or amines), or a mixture of such compounds. The lipid may be polar or non-polar (neutral or zwitterionic) and, if polar, may be one which, in aqueous solution, bears a positive or negative charge. Preferably the lipid is a naturally occurring one such as any of the 100 or so distinct lipids which have been identified as being present in cell membranes especially mammalian and particularly in human cell membranes. As used herein the term "lipid" does not include glycerol esters which are commonly regarded as oils, fats or waxes rather than lipids.

Suitable lipids for use in the present invention will usually fall into one of the following classes: phospholipids, sphingolipids, glycolipids or cholesterol and cholesterol esters, although certain lipids, such as cerebrosides and gangliosides may be classified as both sphingolipids and glycolipids.

A phospholipid contains in its structure a phosphate ester linkage with a glycerol residue and is a diester molecule of long chain acids such as oleic and stearic acids.

The major phospholipids present in cell membranes are the phosphatidylcholines. These particular lipids have been shown to have no influence on blood clotting times when examined in Stypven tests of blood coagulation. However there also occur in some biological membranes small amounts of other lipid molecules, for instance, a phospholipid called Platelet Activating Factor (1) because of its potent platelet aggregation activity (2). This lipid appears to play a major role in various inflammatory and allergic states (3). Another lipid found in natural membranes is Phospholipid Antithromboplastin, so called because of its potent anti-coagulant properties. It is believed that this lipid is an unsaturated phosphatidylserine (4). Although it is generally accepted that negatively charged lipids such as phosphatidylserine are procoagulant whilst those which are electrically neutral, such as the phosphatidylcholines, are not (5), cerebroside sulfate (a negatively charged lipid) has also been tested for anti-atherosclerotic and anti-coagulant activities with positive results (6). Sphingosine lipids have been examined as physiological inhibitors of blood clotting whilst crude bovine brain cephalin and soybean phosphatides act as clot promoting agents (7,8). Another group of phospholipids having important biocharacteristics, providing medical applications for lipid plasticisers are the phosphatidylinositol lipids. The animal phosphatidylinositols, in contrast to the plant phosphatidylinositols which differ in the fatty acids acylating positions 1 and 2 of the glycerol moeity, are reported to be able selectively to kill cultured tumor cells (9,10). Other phospholipids, including phosphatidylinositol or phosphatidylserine from animal origin, synthetic phosphatidic acid, phosphatidyl glycerol or phosphatidylcholine have been shown to be non-cytotoxic.

The lipids used in the present invention may consist of previously extracted and purified natural membrane components or synthetic materials of the same or similar structures.

Of the lipids which may be used in the present invention, particularly suitable or preferred lipids are as follows:

Phospholipids
Lecithins (e.g. from soybean or egg yolk)
α-Lysophosphatidylcholines
α-Lysophosphatidylethanolamines
α-Lysophosphatidylinositols
α-Lysophosphatidylserines
α-Phosphatidic acids
α-Phosphatidylcholines
α-Phosphatidylethanolamines
α-Phosphatidyglycerols
α-Phosphatidylinositols
α-Phosphatidylserines
1-O-Alkyl-2-acetyl-sn-glycero-3-phosphorylcholines
SPHINGOLIPIDS
Ceramides
Gangliosides
Glucocerebrosides
Sphingomyelin
Phytosphingosine
Psychosine
Sphingosine
Sphingosylphosphorylcholine
Sulfatides The amount of lipid included depends upon a number of factors. By controlling the proportion of lipid/polymer, the physical properties of the plastic material can be modulated and if desired, at the same time, by choosing the appropriate type and quantity of lipid or mixture thereof, especially a phospholipid, glycolipid or sphingolipid or a phospholipid and/or sphingolipid and/or glycolipid mixture, the appropriate biocompatibility, thromboresistance, antitumoral activity or other lipid-associated function can be conferred.

As regards biocompatibility and thromboresistance the mere presence of appropriate phospholipids entrapped in the polymer matrix at its interface with biological fluid or tissue can modify the interface providing the appropriate biological effect. This idea is supported by the evidence accumulated in favour of the role played by particular phospholipids in conferring haemocompatible characteristics to plasma membranes of red blood cells and platelets. Such membranes present asymmetric lipid compositions between the inner and the outer surfaces of the cells, the negatively charged phospholipids being located predominately in the inner surface which exhibits high procoagulant activities, whereas the zwitterionic phospholipids found in the outer surface are inactive in coagulation tests. It is believed that this asymmetry may serve to keep the adequate thromboresistance of blood cells. Thus by imitating the lipid composition of these cell surfaces when formulating the plasticisers it will be possible to modify the plastic surfaces thereby producing polymers with some of the natural biomembrane characteristics.

For sustained release of depot formulations it is possible to take advantage of the diffusion of plasticising lipid molecules and their release from the polymer matrix affording the slow release of the lipid into the surrounding tissue of minute amounts of, for instance, highly active phospholipid or sphingolipid ingredients such as the Phospholipid Antithromboplastin material. However a high rate of diffusion and release may not always be desirable and a compromise between total stability and a controlled diffusion rate can be reached in order to provide the required mechanical and biological properties of the implant.

Usually plastics materials according to the invention will contain plasticising lipid at up to 30% by weight of the weight of the polymer and this may be present as the sole plasticiser or in combination with other conventional plasticisers. However with particular plastics and when appropriate for a desired application certain plastics materials according to the invention may contain far higher quantities of plasticising lipid, for instance up to 50% (for example in the case of polyvinyl acetate) and even up to 60% (such as in the case of polystyrene) or 70% (for example in the case of polyvinyl chloride). Other plastics will not accept such large quantities of plasticisers and in some cases (for example with methacrylate polymers) the maximum content of plasticisers may be as low as 2 to 3%.

The minimum quantity of lipid to be included depends upon the particular plastic and lipid in question but should always be sufficient to provide detectable modification of the rheological or other physical properties of the plastic polymer. Typically plastics materials according to the invention will contain at least 0.01% lipid by weight of the polymer, preferably 0.1% and more preferably 0.5%. Usually plasticising lipid will be included at a level considerably above the minimum, for instance 1%, 2% or 5% and, depending upon the desired end use of the plastics material, plasticising lipid may be added at 10%, 15% or 20% by weight of the weight of the polymer. Other ingredients conventionally employed in plastics technology such as other plasticisers, fillers, colourants, UV absorbers, antioxidants and preservatives such as biocides, especially fungicides, may be included at the usual levels but should be chosen to be compatible with the lipid plasticiser and to avoid undesirable or adverse effects in view of the desired end use of the plastics material.

Many considerations as well as the desired end-use of the plastics material must be taken into account when selecting the particular plasticising lipid or lipids to be used and these are discussed below.

Compatibility

The lipid which is to be used has to be tested for compatibility with the host polymer. This may be achieved by grinding and mixing different proportions of lipid-polymer together and trying to produce a homogeneous melt by gradually heating the sample, by use of a suitable solvent to disperse both polymer and plasticiser then evaporating the solvent or by other suitable techniques.

Glass Transition Temperature ($T_g$)

For all compatible mixtures this has to be determined. Differential Scaning Calorimetry (DSC) is one of the best technique to measure this parameter.

Melt Flow Rate

The samples with a glass transition temperature below the ambient may be used as moulding materials and a simple determination of melt flow rate is used to confirm that such compositions can be injection moulded or extruded. The melt flow rate (m.f.r.) is defined as the amount of material, in grams, which would be extruded, under tightly specified conditions of temperature and pressure, in a time of ten minutes. The apparatus used is essentially a dead-weight extrusion plastimeter, operating under conditions of low shear rate. The material is heated within a hardened steel barrel and maintained at an accurately defined and controlled temperature. From this it is extruded through a standard orifice or die by means of a piston loaded with a standard weight. The specified dead load is the total weight of the piston and the standard weight. In practice, the determination of the gravimetric m.f.r. is effected by cutting a number of specimens of the extrudate, extruded over identical time periods and weighing these. From the average weight of these specimens and the extrusion time of each, a simple calculation gives the m.f.r. in grams per ten minutes. Alternatively, the time taken for the piston to travel a given distance may be measured and from this the volume of material extruded in the same time, from which, combined with the melt density of the material at the test temperature, the gravimetric m.f.r. can be easily calculated. In practice this can be done by the following procedure:

A sample weight of 3.5 g of the composition is charged to the barrel of a melt flow grader apparatus (Utility model, Daventest Ltd., England) provided with a die having a circular orifice of 2 mm diameter and 8 mm land length. The barrel is maintained at a temperature 10° C. above the melting point of the polymer. After a 5 min warm-up period a convenient load is applied to the piston which has a weight of 0.16 kg. The melt flow time is calculated as the total time, including the 5 min warm-up period, taken for a total of 2 g of the composition to be extruded through the die.

Tables III and IV provide a guide to the most appropriate test conditions to use when determining the melt flow rate for particular plastics in common use.

TABLE III

| PLASTIC | CONDITIONS |
| --- | --- |
| Acetals | 5, 13 |
| Acrylics | 8, 9 |
| Acrylonitrile-butadiene-styrene | 7 |
| Cellulose esters | 4, 5, 6 |
| Nylon | 11, 17, 18, 19 |
| Polycarbonate | 15 |
| Polychlorotrifluoroethylene | 10 |
| Polyethylene | 1, 2, 4, 5, 6, 14, 21 |
| Polypropylene | 12 |
| Polystyrene | 7, 8, 9, 16 |
| Polyterephthalate | 20 |
| Vinyl acetal | 3 |

TABLE IV

| CONDITIONS | TEMP. °C. | LOAD gr |
| --- | --- | --- |
| 1 | 125 | 325 |
| 2 | 125 | 2160 |
| 3 | 150 | 2160 |
| 4 | 190 | 325 |
| 5 | 190 | 2160 |
| 6 | 190 | 21600 |
| 7 | 200 | 5000 |
| 8 | 230 | 1200 |
| 9 | 230 | 3800 |
| 10 | 265 | 12500 |
| 11 | 275 | 325 |
| 12 | 230 | 2160 |
| 13 | 190 | 1050 |
| 14 | 190 | 10000 |
| 15 | 300 | 1200 |
| 16 | 190 | 5000 |
| 17 | 235 | 1000 |
| 18 | 235 | 2160 |
| 19 | 235 | 5000 |
| 20 | 250 | 2160 |
| 21 | 310 | 12500 |

Mouldings

Those lipid-polymer proportions which conform to the rheological characteristics of a typical moulding material as determined by the foregoing tests will be finally shaped into moulds. To assess the quality of the resultant shaped articles, thermal, electrical and general mechanical properties such as, impact resistance, tensile strength, flexural modulus, low temperature brittleness, friction coefficient, film permeability, film tear resistance, film shrinkage, surface and volume resistivity, may be measured.

The present invention also provides a process for producing a new plastics material as defined above comprising bringing into association a polymer and a lipid as plasticiser therefor. Plastics according to the invention may be produced by conventional techniques for blending solid or liquid materials including known solid state physical mixing techniques such as in a roller mill and by use of dispersions of the materials in a liquid phase such as a solvent which is subsequently evaporated. Such dispersions may be produced by conventional liquid phase mixing technique including use of high or low shear mixers.

The present invention relates to plastics from all three classes, i.e. the thermoplastics, the elastomer plastics and the thermosetting plastics. Although the boundaries between these types are not clear, this division is generally accepted in the plastics art. Thermosplastics and elastomer plastics are readily plasticised, either before or after polymerisation has occurred, by mixing techniques as mentioned above. However it is generally impossible to plasticise thermosetting plastics by such methods because they cannot be dissolved, melted or worked even with heating due to the cross-linking which has occurred to form the three-dimensional structure characteristic of thermosetting plastics. It is normally necessary to include plasticiser either with the monomer or monomer mixture prior to polymerisation or, unless the polymerisation leads directly to a cross-linked thermosetting plastic structure, by admixture with linear or branched polymers prior to a cross-linking step. Addition of the lipid components into the plastic formulation at the early stages of the polymerization is only practicable if the lipid can stand the polymerization conditions and further technological operations in the plastic manufacture without decomposing, reacting or changing its natural structure.

Another possibility for plasticising thermosetting plastics has been discovered for use with lipid plasticisers. This exploits the ability of polymeric materials to absorb small molecules such as lipids by hydrophobic and/or hydrophilic interactions by causing the plasticiser to permeate the three-dimensional structure of the polymer after its formation. This may advantageously be applied to elastomeric plastics as well. Accordingly the present invention further provides a process for modifying the physical properties of a thermosetting or elastomeric plastic body comprising bringing the plastic into contact with a lipid and permitting the lipid to penetrate into the plastic body, preferably until saturated absorption is achieved.

Usually this process will be applied to a shaped article, often one in its final form ready for use. Conveniently the lipid may be used in the form of a solution in a suitable solvent which may be aqueous and/or organic. Solvent, lipid concentration, temperature and time requirements have to be determined to optimize the absorption conditions, but the natural tendency of polymeric materials to absorb lipids, will contribute to achieving the most convenient extent of lipid absorption.

The invention further provides a shaped article formed from a plastic according to the present invention. Such articles may be formed in conventional manner, for instance by extrusion or by injection or other moulding techniques and/or by machining as necessary for the desired end shape and appropriate to the nature of the particular plastic material in question. Suitable articles formed of plastics of the present invention include sustained release or depot formulations, e.g. for surgical implantation or parenteral, nasal, oral, rectal or vaginal administration to human or animals whether for therapeutic or other purposes, and apparatus and devices for biomedical applications such as those mentioned in Table I above.

The invention will now be illustrated by the following Examples.

EXAMPLE 1

Polyvinyl formal, (Formvar 15/95E, MW. 24000–40000, BDH Chemical Ltd. England) supplied as a free flowing powder, has been tested for compatibility with soybean and egg yolk lecithins. In both cases different proportions of lipid and polymer, ranging from 0 to 30% of lipid, were mixed-ground manually and then heated (100° C.) and compressed in a hydraulic press (5 tons) into a circular mould to form disks of 1 mm in section and 13 mm diameter. Polymer and lipid mixtures form perfect homogeneous melts up to a compositions of 30% of lipid. Increasing amounts of lipid lead to a material which has a more fragile and sticky composition.

EXAMPLE 2

Poly-$\beta$-hydroxybutric acid, (MW. 1000000, by light scattering, Sigma USA) isolated from Alcaligenes species. This polymer has been mixed with different proportions of soybean and egg yolk lecithins and shaped into disks using the same procedure used in Example 1. Polymer and lipids were shown to form homogenous melts up to a proportion as high as 50% of lipid material.

EXAMPLE 3

Polyvinyl acetate, (Aldrich, England, high molecular weight, $T_g$ 30° C., d: 1.191) supplied as pellets This polymer was tested for compatibility with soybean and egg yolk lecithins. Solutions of the polymers in ethyl acetate and the lipids in chloroform were brought together, in different proportions, to produce homogenous mixtures of polymer and lipids. After evaporation of the solvents a rubber-like material was obtained. Proportions ranging from 0 to 50% of lipid were tested with similar results.

EXAMPLE 4

Polystyrene, (Aldrich, England, $T_g$ 100° C., $T_m$ 237.5° C., d: 1.047) supplied as pellets. Both soybean and egg yolk lecithin were used as plasticisers for compatibility tests with this polymer. Samples containing different proportions of lipids and polymer were weighted and dissolved in chloroform to produce homogenous mixtures of both components. After evaporating the solvent, rather hard and rigid materials were obtained. Very high proportions (up to 60%) of lipids were admitted by the polymer as plasticisers.

REFERENCES

1. Hanahan, D. J., Demopoulos, C. A., Liehr, J. and Pinckard, R. N., J. Biol. Chem. 255, 5514–5516 (1980).
2. Beneviste, J., Henson, P. M. and Cochrane, C. G., J. Exp. Med. 136, 1356–1377 (1972).
3. Siraginian, R. P. and Osler, A. G., J. Immunol. 106, 1244–1251 (1971).
4. Turner, D. L., Arch. Biochem. Biophys. 77, 249–257 (1958).
5. Zwaal, R. F. A., Biochim. Biophys. Acta 515, 163–205 (1978).
6. Wago, K., Japan Heart J. 2, 354–367 (1961).
7. Hecht, E., , J. Michigan State Med. Soc. 56, 1445 (1957).

8. Goto, M., Rinsho Shoni Igaku 9, 184–202 (1961).
9. Jett, M. and Alving, C. R., Biochim. Biophys. Res. Commun. 114, 863–871 (1983).
10. Myher, J. J. and Kuksis, A., Biochim. Biophys. Acta 795, 85–90 (1984).

I claim:

1. A process for preparing a hemocompatible and thrombo-resistant plastic material consisting only of a polymer and a lipid selected from the group consisting of egg lecithin and α-phosphatidylcholine, comprising the steps of:

(1) admixing by melt blending said lipid with a preformed polymer to produce an admixture wherein said lipid is a simple external plasticizer, the preformed polymer being a thermoplastic material selected from the group consisting of acetals, acrylics, acrylonitrile-butadiene-styrene, cellulose esters, nylon, polycarbonate, polychlorotrifluoroethylene, polyethylene, polypropylene, polystyrene, polyterephthalate and vinyl acetals; and (2) shaping the resulting admixture and forming said plastic material, whereby the hemocompatibility and thrombo-resistance of said plastic material is greater than the hemocompatibility and thrombo-resistance of said polymer, and said plastic material contains said lipid in an amount of at least 0.1% by weight based upon the weight of said polymer.

2. A process for preparing a hemocompatible and thrombo-resistant plastics material comprising a polymer and a lipid, said lipid being selected from the group consisting of egg lecithin and alpha-phosphatidyl choline and being present in the plastics material in an amount of at least 0.1% by weight based on the weight of said polymer, comprising the steps of:

(1) forming a solution or dispersion of said lipid in a solvent;

(2) forming a solution or dispersion in a solvent of said polymer which has been preformed;

(3) mixing said solution or dispersion formed in step (1) with said solution or dispersion formed in step (2) in relative quantities such that the amount of lipid present in the resulting mixture is at least 0.1% by weight based on the weight of said polymer;

(4) blending said mixture formed in step (3); and (5) shaping and forming said plastics material by evaporating said solvent, whereby the hemocompatibility and thrombo-resistance of said plastics material is greater than the hemocompatibility and thrombo-resistance of said polymer.

3. The process according to claim 2, wherein said preformed polymer is selected from the group consisting of cellophane, cellulose acetate, a polyolefin, a fluorinated hydrocarbon, Polyhydroxyethylmethacrylate, polymethylmethacrylate, poly(acrylamide), poly(acrylic acid), poly(acrylonitrile), polyamide resin, poly(1-butene), poly(2,4-butylene terephthalate), poly(butylmethacrylate), poly(tertbutylmethacrylate), poly(4-tertbutyl styrene), polycarbonate resin, poly(cyclohexylmethacrylate), poly(2,6-dimethyl-1,4-phenylene oxide), poly(ethylene), poly(ethylene) chlorinated, poly(ethylene glycol), poly(ethylene oxide), poly(ethylene terephthalate), poly(ethyl methacrylate), nylon, polyimide, poly(isobutyl methacrylate), poly(4-isopropyl styrene), polysulfone resin, poly(tetrafluoro ethylene), poly(vinyl acetate), poly(vinyl alcohol), poly(vinyl butyral), poly(vinyl chloride), poly(vinyl formal), an acrylate elastomer, chlorosulfonated polyethylene, natural rubber, a polyurethane, silicone rubber, polyethylmethacrylate, a polyamide, polyethyleneterephthalate, silk, polymonochloro-p-xylylene, epoxy resin, polyethylene, polypropylene, polyvinylalcohol, and polyvinylidenechloride, mixtures thereof and copolymers comprising repeating units of at least one such polymer.

4. The process according to claim 1, wherein said preformed polymer is an elastomer.

5. The process according to claim 1, wherein the hemocompatible and thrombo-resistant plastic material comprises said lipid in an amount of at least 1.0% by weight of the weight of said polymer.

6. The process according to claim 1, wherein the hemocompatible and thrombo-resistant plastic material comprises said lipid in an amount of up to 30% by weight of the weight of said polymer.

7. The process according to claim 3, wherein said polymer is a thermoplastics polymer selected from the group consisting of cellophane, cellulose acetate, polyolefins, fluorinated hydrocarbons, poly(hydroxyethylmethacrylate), poly(methylmethacrylate), polycarbonates and polyvinylchloride.

* * * * *